Sept. 14, 1954 R. O. RUBEL, JR Plant Pat. 1,303
CAMELLIA PLANT
Filed Sept. 16, 1953
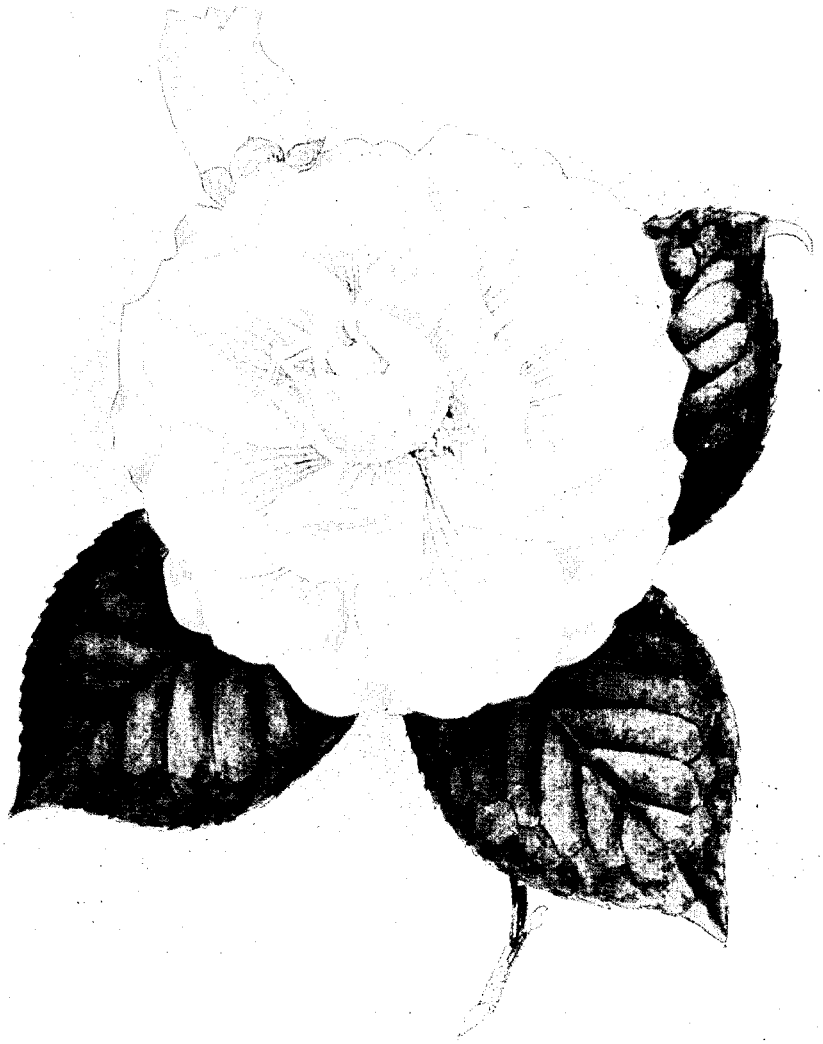
WITNESS
Addison E. Avery
INVENTOR
ROBERT O. RUBEL, JR.
by Rummler, Rummler & Snow,
ATTYS.

Patented Sept. 14, 1954

Plant Pat. 1,303

UNITED STATES PATENT OFFICE 1,303

CAMELLIA PLANT

Robert O. Rubel, Jr., Mobile, Ala., assignor to Cliff Harris, Crichton Station, Mobile, Ala.

Application September 16, 1953, Serial No. 380,637

1 Claim. (Cl. 47—60)

This invention relates to a new and distinct variety of Camellia plant which originated as a sport of a seedling variety known by the name "N. C. Madsen" and also by the name "Mrs. Baldwin Wood" (unpatented).

Cuttings from the "N. C. Madsen" seedling were purchased by me. As these cuttings matured, scions were taken from them and grafted to very old understock. From one of these grafts made from cuttings of the "N. C. Madsen" seedling, this new sport variety occurred. This variety originated at Mobile, Alabama, and has there been asexually reproduced by me.

This new variety differs from the parent variety by the distinctively new color of its bloom which is light orchid with distinct darker orchid veining and with each petal margined with a narrow white strip.

In other respects, this new variety has identical characteristics of form, habits of growth, keeping qualities of bloom and tolerance as its parent. It is a compact, very prolific and winter-hardy plant. The flowers keep exceptionally well and are excellent for florists' corsage flowers. It is a free bloomer that tolerates a wide range of temperatures and has bloomed profusely after a severe freeze. It is especially tolerant to and desirable for arid areas. At my nursery at Mobile, Alabama, it flowers as early as November outdoors and continues blooming through February.

The accompanying drawing shows bloom, bud and foliage in their natural form and closely approaches the natural color of the bloom which has a distinctive orchid cast and veining.

The color designations, according to "A Dictionary of Color by Maerz and Paul" are as follows:

| Part | Plate | Lts. | No. |
|---|---|---|---|
| Flower: | | | |
| Outer edge pure white | 1 | A | 1. |
| shading into | 51 | E | 2. |
| shading into | 51 | F | 3. |
| shading into (darkest tone) | 51 | G | 4. |
| Pistils or stamens (yellow) | 9 | L | 6. |
| Darker veining | 51 | I | 9. |
| Leaves: | | | |
| Top of leaf | 23 | L | 7 plus green. |
| Under side of leaf | 22 | L | Do. |
| Steam | 7 | C | 12. |

The following is a detailed description of my new variety:

Parentage: Sport of "N. C. Madsen."
Classification: Camellia japonica.

The plant has been asexually reproduced by cuttings and graftings at Mobile, Alabama, and its features remain true to form and color.

Flower:

*Recurrent.*—Yes.
*Blooms.*—Midseason to late; prolific bloomer.
*Size.*—4 to 5 in. (11½ to 12½ cm.) wide and 1⅝ in. (4 cm.) high.

*Borne.*—Singly and double.
*Shape.*—High center.

Petalage:

*Number.*—43 to 45.
*Form.*—Loose rose form and sometimes imbricated, when central petals form an unopened conical bud.
*Size.*—$2\frac{3}{16}$ in. (5.5 cm.) long and 1⅜ in. (3.5 cm.) wide.
*Color.*—Light orchid with distinct darker orchid veining, each petal margined with white strip approximately $\frac{1}{12}$ in. (2 mm.) wide.
*Texture.*—Leathery.
*Appearance.*—Satiny. Affected by hot weather, 60° or above. Slight fragrance.
*Lasting quality.*—On plant and cut flower excellent.

Bud:

*Size.*—Large, $1\frac{3}{16}$ in. (3 cm.) long and $\frac{13}{16}$ in. (2 cm.) wide.
*Form.*—Elliptic ovoid.
*Color.*—When sepals first divide, light-green; when petals begin to unfurl, light-green.
*Sepals.*—Completely hooded over bud. 8–10 in number.
*Calyx.*—Large 1⅞ in. (4.5 cm.) across. Shape—cupped. Aspect—smooth. Does not split.

Plant:

*Form.*—Bush, round.
*Height.*—Depends on age.
*Growth.*—Compact, vigorous, branching.

Foliage:

*Quantity.*—Abundant.
*Size of leaf.*—Approximately 3⅜–$4\frac{15}{16}$ in. (8.5–12.5 cm.) and 1⅞–2¾ in. (4.5–7 cm.) wide.
*Texture.*—Leathery; glossy.
*Shape.*—Ovate.
*Petioles.*—Length $\frac{13}{16}$ in. (2 cm.).
*Color.*—Upper side, blue-green. Under side, yellow-green.

Genital organs:

*Stamens.*—Approximately 176. Golden-anthered stamens in direct center of flower. Styles—number 3–4. Length, 1 cm. Pollen—yellow.
*Ovary.*—Glabrous.

Fruit: Fertile.

*Shape.*—Usually ovoid.
*Color.*—At maturity, green.

I claim:

The new and distinct variety of camellia plant substantially as shown and described, characterized particularly by the size and color of its bloom, their keeping qualities and its tolerance to temperature range and to arid conditions.

No references cited.